US009320456B2

(12) United States Patent
Reinstädtler

(10) Patent No.: US 9,320,456 B2
(45) Date of Patent: Apr. 26, 2016

(54) MEASURING HEAD FOR DIAGNOSTIC INSTRUMENTS AND METHOD

(75) Inventor: Jürgen Reinstädtler, Würzburg (DE)

(73) Assignee: CareFusion Germany 234 GmbH, Hoechberg (DE)

( * ) Notice: Subject to any disclaimer, the term of this patent is extended or adjusted under 35 U.S.C. 154(b) by 2794 days.

(21) Appl. No.: 11/539,666

(22) Filed: Oct. 9, 2006

(65) Prior Publication Data

US 2007/0084466 A1    Apr. 19, 2007

(30) Foreign Application Priority Data

Oct. 10, 2005 (EP) ..................................... 05109390

(51) Int. Cl.
*A61B 5/087* (2006.01)
*A61M 16/10* (2006.01)
*A61M 16/20* (2006.01)

(52) U.S. Cl.
CPC .............. *A61B 5/087* (2013.01); *A61M 16/204* (2014.02); *A61M 2016/102* (2013.01); *A61M 2016/103* (2013.01); *A61M 2016/1025* (2013.01)

(58) Field of Classification Search
CPC .............. A61M 16/10; A61M 16/203–16/204; A61M 2016/102–2016/1035; A61B 5/082; A61B 5/083–5/0836
USPC .............. 128/200.24, 204.18, 204.21–204.23
See application file for complete search history.

(56) References Cited

U.S. PATENT DOCUMENTS

| 4,256,100 | A | * | 3/1981 | Levy et al. | 128/204.21 |
|---|---|---|---|---|---|
| 4,285,339 | A | * | 8/1981 | McIntyre | 128/204.23 |
| 5,443,075 | A | | 8/1995 | Holscher | |
| 5,465,712 | A | * | 11/1995 | Malis et al. | 128/205.25 |
| 5,582,163 | A | * | 12/1996 | Bonassa | 128/204.26 |
| 5,657,752 | A | * | 8/1997 | Landis et al. | 128/207.13 |
| 5,918,596 | A | * | 7/1999 | Heinonen | 128/204.21 |
| 6,158,434 | A | * | 12/2000 | Lugtigheid et al. | 128/204.22 |
| 6,390,091 | B1 | * | 5/2002 | Banner et al. | 128/204.21 |
| 6,435,181 | B1 | * | 8/2002 | Jones et al. | 128/204.18 |
| 6,662,803 | B2 | * | 12/2003 | Gradon et al. | 128/205.25 |
| 7,597,100 | B2 | * | 10/2009 | Ging et al. | 128/204.18 |
| 7,845,354 | B2 | * | 12/2010 | Kwok et al. | 128/207.12 |
| 2002/0185126 | A1 | | 12/2002 | Krebs | |
| 2003/0164170 | A1 | * | 9/2003 | Drew et al. | 128/204.18 |
| 2005/0217671 | A1 | | 10/2005 | Fisher et al. | |
| 2007/0095350 | A1 | * | 5/2007 | Darkin et al. | 128/206.24 |

FOREIGN PATENT DOCUMENTS

EP    0659445         6/1995
EP     659445 A1  *  6/1995

* cited by examiner

*Primary Examiner* — Valerie L Skorupa
(74) *Attorney, Agent, or Firm* — McDermott Will & Emery LLP

(57) ABSTRACT

This invention relates to a measuring head which comprises an intake, an outlet, a mouthpiece and an electrically controlled proportional valve. The intake may be connected to a pressurized gas reservoir. The outlet releases exhaled gas and excess gas into the ambient. A mouthpiece provides gas to a subject and accepts exhaled gas from the subject. The electrically controlled, proportional valve is pneumatically connected between said intake and said mouthpiece for controlling the gas flow from said intake to said mouthpiece and said outlet. The invention further relates to a method for controlling a gas flow from the intake to the outlet.

12 Claims, 3 Drawing Sheets

MEASURING HEAD FOR DIAGNOSTIC INSTRUMENTS AND METHOD

CROSS REFERENCE TO RELATED CO-PENDING APPLICATIONS

This application claims the benefit of the European patent (EP) application number 05109390.4 filed on Oct. 10, 2005 and entitled MEASURING HEAD FOR DIAGNOSTIC INSTRUMENTS AND METHOD the content of which is expressly incorporated herein by reference.

FIELD OF THE INVENTION

The present invention relates to pulmonary and cardiopulmonary diagnostic instruments and more specifically to measuring heads for such instruments and a method for controlling gas flow.

BACKGROUND OF THE INVENTION

As described e.g. on the Internet site of the University of North Carolina, school of medicine, Whitehead Medical Society, First Aid for the first year, several parameters can be determined in order to describe the respiratory mechanics and gas exchange of a subject's lung:
  FVC—forced vital capacity—total amount air exhaled
  FEV1—amount of air exhaled during the first second of forced expiration
  FRC—functional residual capacity
  TLC—total lung capacity
  RV—residual volume
  IC—inspiratory capacity—amount of air inhaled above FRC; IC=TLC−FRC
  ERV—expiratory reserve volume—amount of air exhaled below FRC; ERV=FRC−RV FVC, $FEV_1$, IC and ERV may be determined by spirometry. Process begins with patient breathing normally for several cycles. Normal breathing is represented by FRC—the lung volume at which the elastic forces of the lung are equally opposed by the outward pull of the chest wall. Tidal volume is the amount of air inhaled during normal breathing. Then the patient inhales to TLC and exhales forcefully to RV.

FRC may be determined by (whole body) Plethysmography, Helium dilution or Nitrogen washout technique, which are described e. g. in "Respiratory Mechanics in Infants: Physiologic Evaluation in Health and Disease", by a joint committee of the ATS Assembly on Pediatrics and the ERS Paediatrics Assembly, American Review of Respiratory Disease Vol. 147, 1993, p. 475-496.

The nitrogen washout technique is to measure the volume of nitrogen washed out of the lungs when subject rebreathes from a reservoir of nitrogen-free gas. In the original studies the equipment used was fairly simple yet cumbersome to operate, later real-time techniques relied on mass spectrometers, which are technically demanding to maintain. If the amount of washed out nitrogen is measured and the initial concentration of alveolar nitrogen is known, then the lung volume at which the washout started can be derived. If washout starts at FRC, then FRC equals the volume of nitrogen washed out divided by the initial nitrogen concentration in the lungs.

The difficult aspect of this technique is the accurate measurement of the volume of nitrogen washed out. In the two most commonly used methods, the volume of nitrogen is either measured from the expired gas in a collection bag or obtained by continuous integration of nitrogen concentration in the expired gas.

In the expired gas collection method, the expired nitrogen volume is calculated as the product of the nitrogen concentration and the bag volume. Any inaccuracy in the measurement of the bag volume or, more commonly, the final nitrogen washout concentration, will cause significant errors. Because the final nitrogen concentration is very low, having been diluted with large amounts of oxygen, an error of <1% in its measurement will cause substantial error. The resolution, and thus the accuracy, of the method depends on the initial alveolar nitrogen concentration.

Using rapidly responding gas analyzers (or mass spectrometers) to obtain instantaneous nitrogen concentration and a computer to integrate flow signals, an open circuit system can be created. The expired volume and the associated nitrogen concentration are measured continuously by fast response gas analysers or mass spectrometers. A variation of this technique used a constant bias flow, higher than the peak inspiratory flow. This bias flow diluted the expiratory nitrogen concentration and resulted in similar accuracy problems as the collection bag systems.

Furthermore the large continuous bias flow consumed large amounts of oxygen gas, increasing the cost of the test.

Other potential problems with the nitrogen washout technique include those associated with analyzer response time, lag time between flow rate and gas concentration, and sampling rate.

Corrections must be made for the nitrogen flushed from the tissues and blood. The latter usually causes <5% error within a typical washout period of 2 to 3 minutes but may be larger if washout is prolonged in patients with lung disease. In the usual adult methods, end-tidal nitrogen concentration is measured continuously and required to decrease to <2%, because concentrations higher than 2% tend to overlook the effects of extremely slow spaces. Final nitrogen concentrations of <1% tend to exaggerate the effect of normal nitrogen diffusion from pulmonary blood to the alveolar space. In some methods the final concentration is derived from exponential analysis of only a few breaths.

As with all gas dilution techniques, results may be invalidated by leaks.

Further, it is clinically useful (cf. osy-RespNotes.DOC, l.c.) to measure diffusing capacity for carbon monoxide ($D_LCO$). Lung has a large surface area for gas diffusion of about the size of a tennis court and diffusion barrier is very small (0.1 Mm-1.0 Mm). CO is used because its uptake rate is limited only by diffusion process even in the normal lung. However, patients with low hemoglobin levels will have falsely low $D_LCO$ and a correction factor is used. Diseases that affect thickness of diffusing surface (emphysema, interstitial fibrosis) are notable for low $D_LCO$. Diffusion capacity for CO=volume of CO transferred in milliliters/minute per mmHg of alveolar gas pressure $D_LCO=V_{CO}/P_ACO$; $V_{CO}$ is the rate of CO uptake and a measure difference between known concentrations inhaled and amount exhaled after 10 seconds.

In all washout, dilution or diffusion techniques it is important that subject breathes a gas with well-defined composition and is able to exhale gas for immediate analysis or storage and delayed analysis. The inspiratory gas flow control may be performed by so-called demand valves. Compared to inspiratory bag solutions, they offer reduced gas consumption, less potential for inspiratory gas composition deviations due to leaks and easier handling.

Mechanical embodiments of demand valves are also used for diving or resuscitator equipment. In typical mechanical demand valves, the breathing of the subject causes a pressure difference which bends a membrane. The bent membrane opens a valve to a pressurized air or oxygen reservoir. From the pressure difference and the gas flow through the valve a flow resistance may be calculated. A high flow resistance reduces compliance of subjects with necessary maneuvers for washout, dilution or diffusion techniques.

The pressure drop in a tube can be calculated from the following formula (Technische Strömungsmechanik 1, VEB Deutscher Verlag für Grundstoffindustrie, Leipzig):

$$\Delta p = \xi \frac{\rho}{2} v^a = \frac{\lambda l}{d} \cdot \frac{\rho}{2} v^a \quad (1)$$

$\Delta p$ thereby is the pressure dropping in the tube, $\xi$ is a pressure loss correction value of the tube, $\lambda$ is a pipe friction value of the tube, l is the length of the tube, d is the diameter of the tube, $\rho$ is the density of the flowing medium, i.e. approximately 1.2 kg/m$^3$ for air, and v is the flow velocity averaged over the cross-section. a has the value 2 for turbulent flows and 1 for laminar flows. In practice a may also adopt intermediate values, as an ideal-typical form of flow is rare. Equation (1) is also known from Strömungslehre, J. H. Spurk, 4$^{th}$ Edition, Springerverlag, Berlin 1996, wherein $\lambda$ here is called the flow resistance coefficient. The averaged flow velocity is connected with the air flow $\dot{V}$ as follows:

$$\dot{V} = v \cdot \pi \cdot (d/2)^2 \quad (2)$$

V itself stands for an air volume. The point designates the derivative with respect to time d/dt.

If one inserts (2) in (1), one obtains the following quadratic dependence of the pressure drop $\Delta p$ on $\dot{V}$. The dependencies of $\lambda$, l, d and $\rho$ were combined to the constant C, with C being a parameter for the used tube:

$$\Delta p = C \cdot \dot{V}^a \quad (3)$$

$$\dot{V} = C' \Delta p^{1/a} \quad (4)$$

Equation (4) is equivalent to equation (3), but solved for $\dot{V}$.

The WO 98/31282 A1 corresponding to U.S. 2002/0185126 A1 and DE 197 46742 A1, discloses a controlled gas-supply system. Gas sources provide $O_2$, NO, $N_2$He or $CO_2$ under an excess pressure. The flow of each gas source is controlled by a valve, which may in turn be controlled by a pressure sensor close to the nose of a patient. The pressure drop at the beginning of the inspiration may be used as a trigger signal for a valve control.

It is desirable to provide a measuring head and a method for controlling gas flow that combine increased subject's comfort with moderate gas consumption.

SUMMARY OF THE INVENTION

According to an embodiment of the invention a measuring head comprises an intake, an outlet, a mouthpiece and an electrically controlled, proportional valve. The intake is connected to a pressurized gas reservoir. The outlet releases exhaled gas and excess gas into the ambient. The mouthpiece provides gas to a subject and accepts exhaled gas from the subject. The mouthpiece is pneumatically connected to the outlet. The proportional valve is pneumatically connected between the intake and the mouthpiece and controls the gas flow from the intake to the mouthpiece and the outlet.

According to another embodiment of the invention a method for controlling a gas flow from an intake to an outlet and a mouthpiece by a measuring head is provided. The method comprises generating an electrical signal which has a monotonic dependence from the gas flow caused by inhaling of a subject. Further an opening of a proportional valve between the intake and the outlet and the mouthpiece is controlled by the signal. The gas flow caused by inhaling is compensated.

A flow sensor advantageously may serve two purposes at the same time: determine the volume of the inhaled or exhaled gas and optimizing the position of the electrically controlled proportional valve.

A measuring head comprising a flow sensor for measuring the gas flow through a mouthpiece facilitates the calibration of the proportional valve. The additional hardware is limited to a cap or shutter for closing the outlet.

Also a differential pressure sensor may ensure that subject breathes a well-defined gas mixture only. Pressure sensors are less expensive than flow sensors.

An array of on/off solenoid valves may be less expensive than a proportional valve.

Setting the ratio of the flows through two open solenoid valves to a power of two advantageously minimizes the number of solenoid valves for a given ratio of maximum flow divided by flow step size.

The signal of a pressure sensor which measures the pressure at a position between the intake and the proportional valve advantageously enables a balancing of pressure variations at the intake.

BRIEF DESCRIPTION OF THE DRAWING

This invention can be more fully understood from the following detailed description when taken in conjunction with the accompanying drawings, in which.

DETAILED DESCRIPTION OF THE INVENTION

Figure 1:
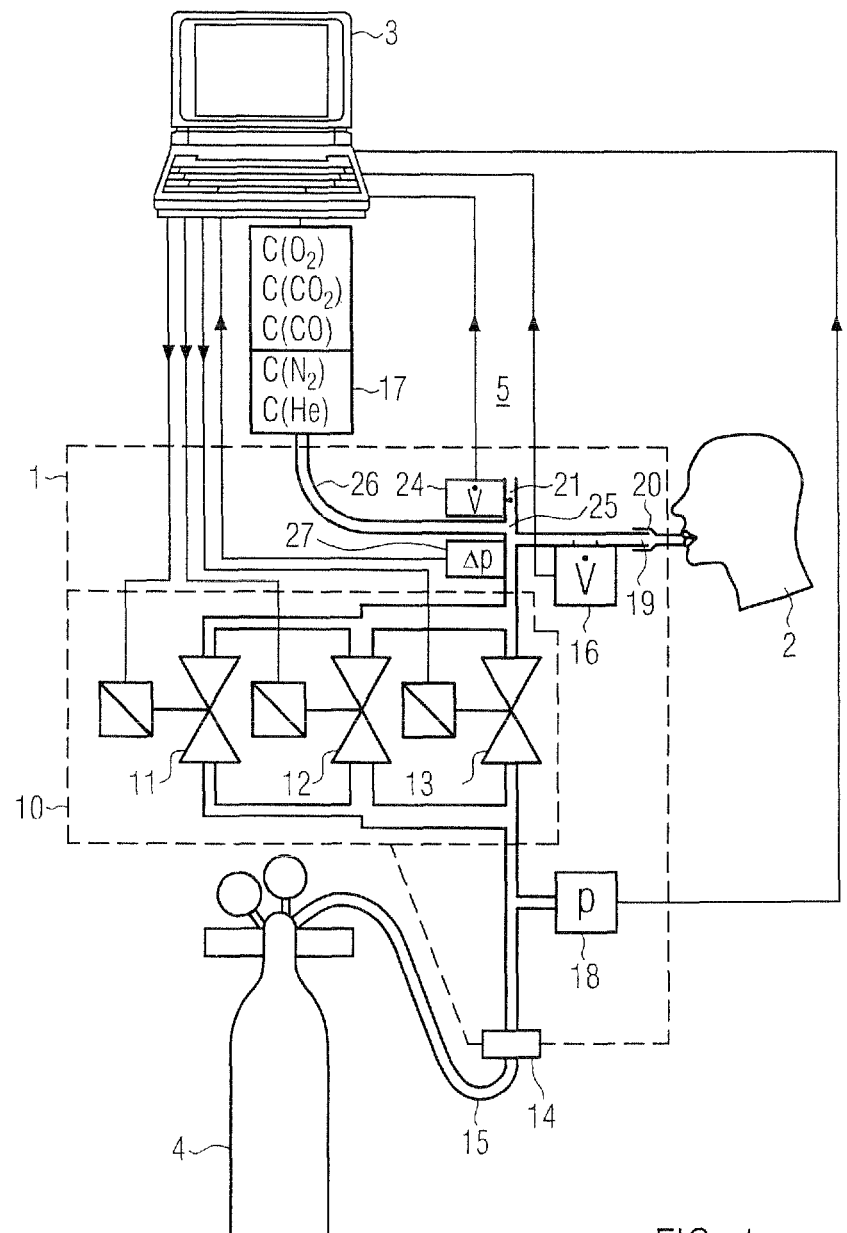
FIG. 1 shows a first embodiment of a pulmonary diagnostic instrument according to the invention.

While the present invention is described with reference to the embodiments as illustrated in the following detailed description as well as in the drawings, it should be understood that the following detailed description as well as the drawings are not intended to limit the present invention to the particular illustrative embodiments disclosed, but rather the described illustrative embodiments merely exemplify the various aspects of the present invention, the scope of which is defined by the appended claims.

FIG. 1 shows a first embodiment of a pulmonary diagnostic instrument. A measuring head 1 controls the gas flow from a pressurized gas reservoir to a subject 2. The pressurized gas reservoir may consist of one cylinder 4 or on an array of cylinders. A single cylinder may be mechanically attached to the diagnostic instrument and connected by a tube to connector 14, which constitutes an intake or measuring head 1. However, the tube shown in FIG. 1 is meant to represent a hospital gas supply 15. A pressure reducer reduces the pressure of 5 to 200 bar within the cylinder to about 4 bar (58 psi) within the hospital gas supply 15.

The gas flow from connector 14 to an outlet 21 and a mouthpiece 19 is controlled by a proportional valve 10. FIG.

1 shows a digital embodiment of proportional valve 10 which comprises three on/off solenoid valves 11, 12 and 13. Solenoid valves are also referred to as magnetic valves. The flow through the solenoid valves 11, 12 and 13 may be adjusted by the length and thickness of the connection tubes and approximately calculated from equations (1) and (2). The gas flow depending on the pressure at connector 14 and the state of the solenoid valves is illustrated in FIG. 3. The connection tubes shown in FIG. 1 to solenoid valves 13, 12 and 11 are short and thick, longer and thick, and longest and thin, respectively. The target values of the flow ratios of the flows through valves 12 and 11 and valves 13 and 12 are 2. Since the relationship between flow and pressure difference is non-linear (confer equation (3)), the ratios may be set exactly to 2 only for a specified pressure difference e. g. 4 bar. On the other hand, edges may have a big influence on the flow. Consequently the actual flow values should be calibrated by a method which is explained in more detail in connection with FIG. 2.

A flow sensor 16 measures the correctly signed gas flow of gas inhaled and exhaled by the subject 2. A mouthpiece top 20 may be provided in order to avoid direct contact between the subject 2 and the mouthpiece 19. The mouthpiece top 20 may be easily detached sterilized. By integrating the signal of flow sensor 16 over time, the volume of inhaled and exhaled air is determined.

For Helium dilution and Nitrogen washout technique and diffusing capacity measurement using CO, the exhaled gas must be analyzed. This is illustrated by gas sensor 17. Gas sensor 17 may be a mass spectrometer connected by a capillary 26 to the junction 25 between outlet and mouthpiece or an array of gas sensors. As illustrated in FIG. 1, a mass spectrometer may determine the concentrations (c) of He, $N_2$, CO, $CO_2$ and $O_2$. In case of the nitrogen washout technique, an $O_2$ and a $CO_2$ sensor may be used. The nitrogen concentration and the concentration of other inert gases is the difference to 100%. The $O_2$ and $CO_2$ concentrations may be also measured during inspiration either for recalibrating the gas sensors, leak detection or verifying minimum gas flow.

During breathing maneuvers of subject 2 the gas flow delivered by proportional valve 10 must be higher than the inspired gas flow. The excess gas flows into the ambient 5 through outlet 21. This is the only way to guarantee that subject 2 inspires a well-defined gas mixture. The short tube between junction 25 and outlet 21 which is about 5 cm long, ensures proper gas flow and prevents back diffusion of ambient air. An additional flow sensor 24 may be provided in order to verify an excess gas flow into the ambient. Flow sensor 24 may measure only the absolute value of the gas flow. A drop of the gas flow below a threshold slightly above 0 indicates a possibly wrong measurement.

If the pressure at connector 14 and the characteristic (confer FIG. 3) of digital proportional valve 10 is known, the flow through valve 10 may be calculated. The proportional valve 10 is opened in order to ensure a minimum excess gas flow through outlet 21 into the ambient 5 throughout breathing maneuvers. This means that the proportional valve 10 is set that the calculated flow through the proportional valve 10 is higher than the inspiratory gas flow measured by flow sensor 16 plus a minimum excess flow. If flow sensor 24 is provided, the proportional valve 10 may be set that the flow measured by flow sensor 24 does not drop below a threshold.

Alternatively or in addition to flow sensors 16 and 24 a differential pressure sensor may be provided. Differential pressure sensor 27 measures the pressure difference between the pressure at junction 25 and the pressure of the ambient air and provides the measurement result to computer 3. The solenoid valves 11, 12 and 13 may be controlled that the pressure at junction 25 exceeds the ambient air pressure by a predetermined value which is greater than or equal to zero. This ensures that the subject 2 inspires a well-defined gas mixture. In the absence of flow sensors 16 and 24 a collection bag may be connected to outlet 21 in order to collect the expired gas and determine its volume and composition.

If the pressure at connector 14 is reasonably constant, there is no need to measure this pressure. However, depending on the flow through the hospital gas supply 15 and the pressure reducer, the pressure provided by the hospital gas supply may easy drop by 30%. In order to allow for such pressure variations pressure sensor 18 is provided.

All components shown in FIG. 1 are either read out or controlled by computer 3, which provides a easy-to-use user interface. Consequently it is no problem to handle two-dimensional, nonlinear proportional valve characteristics.

Figure 2:
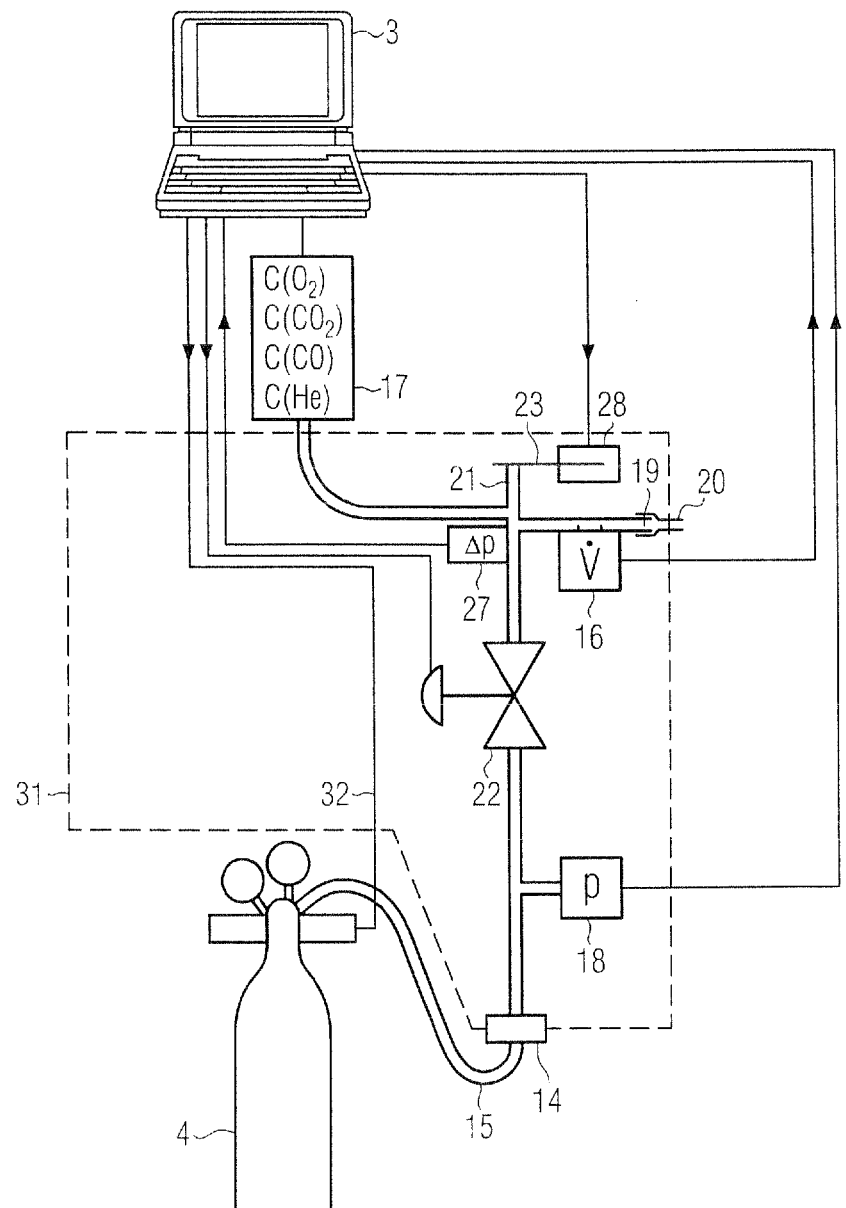
FIG. 2 shows a second embodiment of a pulmonary diagnostic instrument according to the invention.
Figure 3:
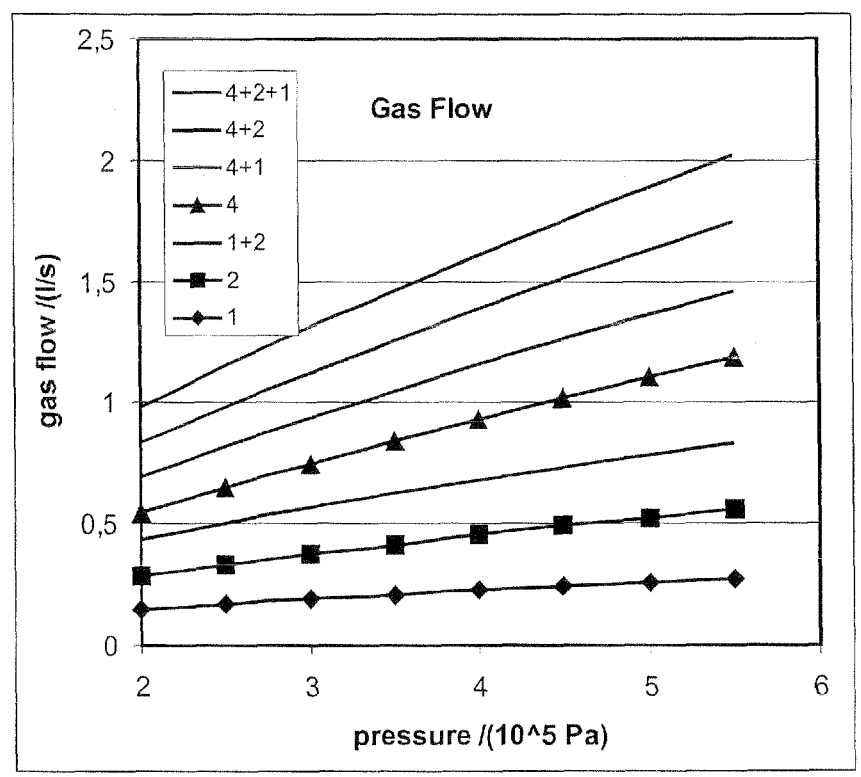
FIG. 3 shows a characteristic of a digital proportional valve.

FIG. 2 shows a second embodiment of the invention, which is slightly different from the first embodiment. The digital proportional valve 10 is replaced by a conventional (analog) proportional valve 22. The advantage of a conventional proportional valve 22 is that the excess gas flow can be controlled more accurately. The disadvantage is its higher price.

In addition to the elements shown in FIG. 1, a shutter 23 and a shutter driver 28 are shown in FIG. 2. The shutter driver 28 is controlled by computer 3. In case differential pressure sensor 28 measures a pressure difference lower than a threshold, which is caused by inspiration of the subject, computer 3 has the shutter 23 closed by the shutter driver 28. During the expiration phase the shutter is re-opened. The threshold is chosen close to zero.

The closing of the shutter 23 during inspiration most reliably prevents the subject from breathing ambient air which devaluates the measurement. The shutter 23 even prevents diffusion. In order to further improve the measurement quality, the threshold may be chosen slightly negative. Alternatively, in order to increase subject comfort and compliance, the threshold may be chosen slightly positive. In order to improve time behavior, the time derivative of the differential pressure may be weighted by a factor and be added to the differential pressure before comparing the result to the threshold.

A shutter may also be used in connection with a digital proportional valve 10. However, this digital proportional valve should have a higher resolution than approximately ⅛ of the maximum flow, which is the resolution the valve 10 shown in FIG. 1.

Moreover, FIG. 2 illustrates the calibration of proportional valve 22, which is also applicable to digital proportional valve 10. Shutter 23 closes outlet 21 during calibration. Consequently, flow sensor 16 measures the gas flow through proportional valve 22. The gas flow is measured at different positions of proportional valve 22 resulting in a one-dimensional characteristic.

In order to take pressure variations at connector 14 into consideration, the gas flow through proportional valve 22 maybe measured at different pressures at connector 14. This is illustrated by control line 32 to the pressure reducer of cylinder 4. In another embodiment, the pressure reducer may be operated manually and a key may be depressed after a new pressure has been set. This results in a two-dimensional flow characteristic as shown in FIG. 3.

Just for the purpose of calibration, the shutter 23 may be replaced by a simple cap that is mounted manually during calibration.

FIG. 3 shows a simulation of a flow characteristic of a digital proportional valve 10 based on equation (4). The measurement points are marked by triangles, squares and diamonds. The pressure has been varied from 2 to 5.5 bars in 0.5 bar steps. Line 1 interpolates the diamonds representing the flow through solenoid valve 11 while valves 12 and 13 are closed. Line 2 interpolates the squares representing the flow through solenoid valve 12 while valves 11 and 13 are closed. Line 4 interpolates the triangles representing the flow through solenoid valve 13 while valves 11 and 12 are closed. The following constants were used for the stimulation:

|   | line/valve | | |
|---|---|---|---|
|   | 1 | 2 | 4 |
| C' | 0.22 | 0.396 | 0.704 |
| A | 1.7 | 1.5 | 1.3 |

The lines designated by 1+2, 4+1, 4+2 and 4+2+1 have been obtained by adding the gas flows of lines 1, 2 and/or 4. The lines of the graph have the same order as lines in the legend. In a real embodiment, only lines 1, 2 and 4 may be measured. In an alternate embodiment all seven lines corresponding to all valve combinations in which at least one valve is open maybe measured.

The maximum flow reaches 3.5 l/s at 4 bar. Line 41 represents a real pressure measured by pressure sensor 18 which is 3.8 bar. Line 42 represents the flow measured by flow sensor 16, which is approximately 1.2 l/s. Under these circumstances computer 3 will open valves 11 and 12, which will result in a flow 43 of 1.45 l/s on line 1+2. Consequently, the excess flow will be 0.25 l/s If, as in this example, pressure values do not exactly match measured values, well-known interpolation algorithms may be performed by computer 3.

Skilled persons will appreciate that a similar characteristic can be obtained for a conventional analog proportional valve 22.

Further modifications and variations of the present invention will be apparent to those skilled in the art in view of this description. Accordingly, this description is to be construed as illustrative only and is for the purpose of teaching those skilled in the art the general manner of carrying out the present invention. It is to be understood that the forms of the invention shown and described herein are to be taken as the presently preferred embodiments.

REFERENCE LIST 1 measuring head
2 subject
3 computer
4 cylinder
5 ambient
10 proportional valve
11, 12, 13 on/off solenoid valves
14 connector/intake
15 hospital gas supply
16 flow sensor
17 gas sensor
18 pressure sensor
19 mouthpiece
20 mouthpiece top
21 outlet
22 proportional valve
23 shutter
24 flow sensor
25 junction
26 capillary
27 differential pressure sensor
28 shutter driver
31 measuring head
32 line
40 two-dimensional gas flow array
41 inlet pressure
42 inspiratory flow
43 estimated gas flow

What is claimed is:

1. A measuring head for diagnosing a pulmonary condition of a subject using a pressurized gas reservoir, comprising:
    an intake for being connected to the pressurized gas reservoir;
    an outlet for releasing exhaled gas and excess gas into the ambient;
    a mouthpiece for providing gas to the subject for inhalation and accepting exhaled gas from said subject, said mouthpiece being pneumatically connected to said outlet and comprising a flow sensor for measuring the flow of said inhaled gas by and exhaled gas from said subject;
    an electrically controlled, proportional valve, which is pneumatically connected between said intake and said mouthpiece for controlling the gas flow from said intake to said mouthpiece and said outlet;
    a computer being electrically connected to said flow sensor and said proportional valve; said computer being programmed for adjusting said proportional valve, such that the gas flow delivered by said proportional valve is higher than the inspired gas flow.

2. The measuring head of claim 1, further including a pressure sensor for measuring the pressure of said inhaled gas by and exhaled gas from said subject.

3. The measuring head of claim 1, wherein said electrically controlled, proportional valve comprises a plurality of on/off solenoid valves.

4. The measuring head of claim 3, wherein a ratio of the flows through said open solenoid valves at a predetermined pressure difference between said intake and said ambient is approximately a power of two.

5. The measuring head of claim 1, wherein said measuring head comprises a pressure sensor which is pneumatically connected to a connection tube between said intake and said proportional valve.

6. A method for controlling a gas flow from an intake to an outlet and a mouthpiece by measuring head, the method comprising:
    generating an electrical signal having a monotonic dependence from the gas flow caused by inhaling of a subject; and
    controlling an opening of a proportional valve between said intake and said outlet and said mouthpiece by said signal such that the gas flow delivered by said proportional valve is higher than the inspired gas flow.

7. The method of claim 6, wherein said electrical signal is generated by a flow sensor and said flow sensor measures the gas flow through said mouthpiece.

8. The method of claim 6, further including measuring a pressure at said intake.

9. The method of claim 8, further comprising:
    closing said outlet; and
    obtaining a two-dimensional gas flow array while said outlet is closed by:
        applying several different pressure values at said intake;
        performing the following at each pressure value:
            adjusting several different openings at said proportional valve; and
            measuring of the gas flow through said mouthpiece.

10. The method of claim 9, further comprising:
    obtaining an estimated gas flow through said intake based on a two-dimensional gas flow array, the pressure at said intake and the opening of said proportional valve; and adjusting the opening of said proportional valve such that said estimated gas flow exceeds said gas flow caused by inhaling.

11. A pulmonary diagnostic instrument, comprising:
a measuring head comprising:
   an intake for being connected to a pressurized gas reservoir;
   an outlet for releasing exhaled gas and excess gas into the ambient;
   a mouthpiece for providing gas to a subject and accepting exhaled gas from said subject, said mouthpiece being pneumatically connected to said outlet; said mouthpiece comprising a flow sensor for measuring the flow of said inhaled gas by and exhaled gas from said subject; and
   an electrically controlled, proportional valve pneumatically connected between said intake and said mouthpiece for controlling the gas flow from said intake to said mouthpiece and said outlet;
the pulmonary diagnostic instrument further comprising:
a computer being electrically connected to said flow sensor and said proportional valve; said computer being programmed such that it suitable for adjusting said proportional valve such that the gas flow delivered by said proportional valve is higher than the inspired gas flow.

12. A measuring head, comprising:
an intake for being connected to a pressurized gas reservoir, said intake being pneumatically connected to a junction;
an outlet for releasing exhaled gas and excess gas into the ambient, said outlet being pneumatically connected to the junction;
a mouthpiece for providing gas to a subject for inhalation and accepting exhaled gas from said subject, said mouthpiece being pneumatically connected to said outlet, said mouthpiece comprising a flow sensor for measuring the flow of said inhaled gas by and exhaled gas from said subject; and
an electrically controlled, proportional valve, which is pneumatically connected between said intake and said mouthpiece for controlling the gas flow from said intake to said mouthpiece and said outlet.

* * * * *